United States Patent [19]

Dickoré et al.

[11] 4,447,635
[45] May 8, 1984

[54] N-SUBSTITUTED IMIDO-DICARBOXYLIC ACID DIARYL ESTER COMPOUNDS AND HERBICIDE INTERMEDIATES

[75] Inventors: Karlfried Dickoré, Leverkusen; Engelbert Kühle, Berg.-Gladbach, both of Fed. Rep. of Germany

[73] Assignee: Bayer Aktiengesellschaft, Leverkusen, Fed. Rep. of Germany

[21] Appl. No.: 393,572

[22] Filed: Jun. 30, 1982

Related U.S. Application Data

[63] Continuation of Ser. No. 233,248, Feb. 10, 1981, abandoned.

[30] Foreign Application Priority Data

Feb. 20, 1980 [DE] Fed. Rep. of Germany ....... 3006226

[51] Int. Cl.³ .......................................... C07C 125/063
[52] U.S. Cl. ......................................... 560/115; 71/93; 260/465 D; 544/223; 546/309; 546/335; 548/163; 548/180; 549/424; 549/480; 549/426; 549/493; 560/22; 560/29; 560/31; 560/32; 560/132; 560/134; 560/137
[58] Field of Search ............... 560/115, 132, 134, 137; 260/465 D

[56] References Cited

U.S. PATENT DOCUMENTS

3,857,860 12/1974 Kühle et al. .................... 560/29 X
4,014,923 3/1977 Kühle et al. .................... 560/29 X

FOREIGN PATENT DOCUMENTS

2132936 1/1973 European Pat. Off.
484683 5/1938 United Kingdom.

OTHER PUBLICATIONS

Tompkins et al., Journal of the American Chemical Society, vol. 69 (1947), pp. 2616-2618.
Houben-Weyl, Methoden der Organischen Chemie, vol. VIII, Part III, (1952), pp. 138 & 203.

*Primary Examiner*—Richard Raymond
*Attorney, Agent, or Firm*—Felfe & Lynch

[57] ABSTRACT

Novel N-substituted imido-dicarboxylic acid diaryl ester compounds of the general formula

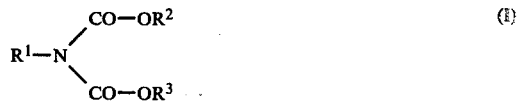

in which
R¹ represents an optionally substituted aliphatic, cycloaliphatic, araliphatic, aromatic, heterocyclic radical and
R² and R³ can be identical or different and represent an optionally substituted aryl radical, and a process for their preparation characterized in that a carbamic acid aryl ester of the general formula

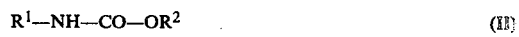

in which R¹ and R² have the abovementioned meanings, is reacted with a carbonic acid aryl ester halide of the general formula

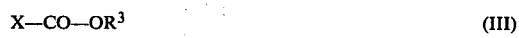

in which
R³ has the abovementioned meaning and
X represents a halogen atom, optionally in the presence of a diluent, optionally at a temperature between 100° and 300° C.

The new compounds (I) can be used as intermediate products for the preparation of known herbicidal active compounds from the 1,3,5-triazine,2,4-(1H,3H)-dione series.

13 Claims, No Drawings

N-SUBSTITUTED IMIDO-DICARBOXYLIC ACID DIARYL ESTER COMPOUNDS AND HERBICIDE INTERMEDIATES

This is a continuation application of U.S. Ser. No. 233,248 filed Feb. 10, 1981, now abandoned.

This invention relates to certain N-substituted imido-dicarboxylic acid diaryl ester compounds and to a process for their preparation. In additional aspects, the invention relates to the use of such compounds as intermediate products, and processes, for the synthesis of herbicides.

The invention provides, as new compounds, the N-substituted imido-dicarboxylic acid diaryl ester compounds of the formula

(I)

in which
R$^1$ represents an optionally substituted aliphatic; cycloaliphatic, araliphatic, aromatic, heterocyclic radical and
R$^2$ and R$^3$ can be identical or different and represent an optionally substituted aryl radical.

The present invention further provides a process for the production of compounds of the present invention characterised in that a carbamic acid aryl ester of the general formula

(II)

in which
R$^1$ and R$^2$ have the abovementioned meanings, is reacted with a carbonic acid aryl ester halide of the general formula

(II)

in which
R$^3$ has the abovementioned meaning and
X represents a halogen atom, optionally in the presence of a diluent, optionally at a temperature between 100° and 300° C.

It is to be described as suprising that the reaction according to the invention proceeds, since carbamic acid aryl esters do not react with carbonic acid aryl ester halides in the desired manner in the presence of an acid-binding agent: it is indeed known that N-substituted dialkyl imido-esters can be prepared by reacting N-substituted carbamic acid alkyl esters with carbonic acid alkyl ester chlorides in the presence of metallic sodium (see J. Amer. Chem. Soc. 69, 2616–2618 (1947).

However, attempts to apply this method to the corresponding aryl esters fail completely. For example, neopentyl-carbamic acid phenyl ester reacts with carbonic acid phenyl ester chloride under the reaction conditions according to the state of the art to give exclusively neopentyl isocyanate and diphenyl carbonate. Even with butyl-lithium as the acid-trapping agent, no neopentylimido-dicarboxylic acid diphenyl ester is formed. It is all the more suprising that the reaction according to the invention proceeds smoothly at elevated temperature and in the absence of an acid-trapping agent. According to the state of the art, it would have been expected that total re-splitting of the carbamic acid aryl ester employed into isocyanate and phenol would take place (see Houben-Weyl: Methoden der organischen Chemie (Methods of Organic Chemistry), 4th Edition. Volume 8, page 127 (1952)).

If neopentyl-carbamic acid phenyl ester and carbonic acid phenyl ester chloride are used as starting substances, the course of the reaction can be represented by the following equation:

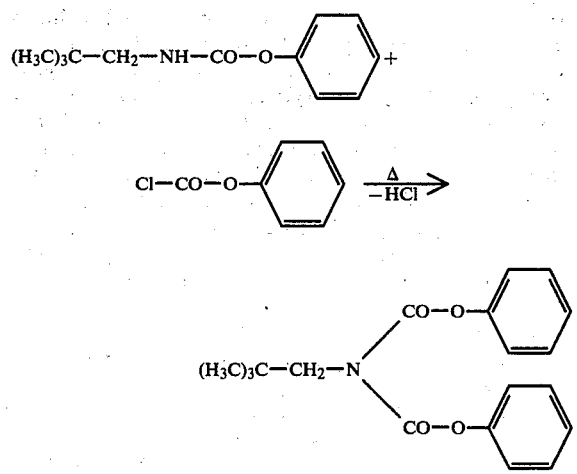

Preferred compounds of the present invention and starting substances of formula (I) are those in which R$^1$ represents a straight-chain or branched alkyl radical which has 1 to 10 carbon atoms and is optionally substituted by lower alkoxy, lower alkylmercapto, halogen (in particular chlorine), cyano or nitro; an alkenyl radical with 3 to 8 carbon atoms; an alkinyl radical with 3 to 8 carbon atoms; a cycloaliphatic radical which has 5 to 8 ring carbon atoms and can optionally be substituted by lower alkyl; an araliphatic radical with a total of 7 to 12 carbon atoms, it being possible for the aromatic ring system optionally to be substituted by halogen, nitro, trifluoromethyl, cyano, lower alkyl and/or lower alkoxy; an aromatic radical which has 6 to 12 carbon atoms and optionally substituted by halogen, nitro, trifluoromethyl, cyano, lower alkyl and/or lower alkoxy, or a heterocyclic radical with 5 or 6 ring atoms, it being possible for 1 to 3 hetero-atoms, such as oxygen, sulphur and/or nitrogen, to be present in the ring system, R$^2$ represents a phenyl or naphthyl radical which is optionally substituted by chlorine, methyl and/or methoxy and, in the case of compounds of the present invention, R$^3$ independently of R$^2$ has any of those meanings given for R$_2$.

The expressions "lower alkyl", "lower alkoxy" and "lower alkylmercapto" in the context of this invention are intended to denote appropriate radicals with in each case 1 to 4 carbon atoms.

The carbamic acid aryl esters of the formula (II) used in the process of the present invention are already known, or they can be prepared by known processes, by addition of isocyanates onto phenols (see Houben-Weyl, Methoden der organischen Chemie (Methods of Organic Chemistry), 4th Edition, Volume 8, page 142 (1952)) or by reaction of carbonic acid aryl ester chlorides with primary amines (see Houben-Weyl, Methoden der organischen Chemie (Methods of Organic Chemistry), 4th Edition, Volume 8, page 138 (1952)).

The starting compounds of the formula (II) can furthermore be prepared by reacting carbonic acid diaryl esters with amines (see Preparative Example 5b; see also Houben-Weyl, Methoden der organischen Chemie (Methods of Organic Chemistry), 4th Edition, Volume 8, page 139 (1952)).

Specific examples of starting compounds of the formula (II) which may be mentioned are: the phenyl esters of methyl-carbamic acid and also of 2-chloroethyl-, isopropyl-, tert.-butyl-, sec.-butyl-, iso-butyl-, tert.-pentyl, neo-pentyl-, 1,2,2-trimethylpropyl-, 2,2,2-trifluoroethyl-, 2-ethoxyethyl-, 2-ethyl-mercaptoethyl-, ω-cyanohexyl-, allyl-, propargyl-, cyclopentyl-, cyclopropylmethyl-, cyclopentylmethyl-, cyclohexylmethyl-, (2,5-methano-cyclohexyl)-methyl-, cycloheptylmethyl-, cyclododecanylmethyl adamantylmethyl-, 2-furylmethyl-, 2-pyranylmethyl-, 2-pyridylmethyl-, 3-pyridylmethyl-, 4-pyridylmethyl-, 2-methylpentyl-, 2-ethylpentyl-, 2-methylhexyl-, 2-ethylhexyl-, 2-methylcyclohexyl-, benzyl-, 4-chlorobenzyl-, 4-nitrobenzyl-, phenethyl-, phenyl-, 4-chlorophenyl-, 3,5-dichlorophenyl-, 3,4-dichlorophentyl-, 3-trifluoromethyl-, 2-chloro-4-nitrophenyl-, 3-tolyl-, 4-ethylphenyl-, 3-anisidyl-, 1-naphthyl-, 2-furyl-, 4-pyridyl- and 2-benzthiazolylcarbamic acid.

Preferred carbonic acid aryl ester halides of formula (II) to be used as starting substances are those in which $R^3$ independently of $R^2$ in the starting substance of formula (II) represents a phenyl or naphthyl radical which is optionally substituted by chlorine, methyl and/or methoxy and X represents a chlorine or fluorine atom.

The carbonic acid aryl ester halides of the formula (III) used in the process of the present invention are known, or they can be prepared by known processes. Thus, for example, the carbonic acid phenyl ester chlorides can be prepared in a manner which is in itself known, by phosgenation of phenols (see Houben-Weyl, Methoden der organischen Chemie (Methods of Organic Chemistry), 4th Edition, Volume 8, page 103 (1952)); the corresponding carbonic acid phenyl ester fluorides can be obtained analogously from phenols and difluorophosgene (see J. Cjem. Soc. [London] 1948, page 2183).

Specific examples of starting compounds of the formula (III) which may be mentioned are: the carbonic acid ester chlorides of phenol, 4-chlorophenol, 4-cresol and 1-naphthol and the carbonic acid ester fluoride of phenol.

The reaction according to the invention can be carried out in the absence or in the presence of a diluent. If no diluent is used, it is most appropriate to add the carbamic acid aryl ester of formula (II) in the molten form to the carbonic acid aryl ester halide of formula (III), which is in the reaction vessel and has been warmed to the reaction temperature. This embodiment is possible and particularly advantageous in those cases where the carbamic acid aryl ester of formula (II) to be employed is completely stable at its melting point (see Example 5b).

Possible diluents for the carbonic acid aryl ester halide of formula (III), which is in general initially introduced, are high-boiling inert organic solvents, such as chlorinated or nitrated aromatic hydrocarbons (for example chlorobenzene, the dichlorobenzenes, the trichlorobenzenes or nitrobenzene). Low-boiling inert organic solvents, such as hydrocarbons and chlorinated hydrocarbons (for example petroleum ether, cyclohexane, chloroform, difluorodichloromethane, or, preferably, methylene chloride) can appropriately be used as diluents for the carbamic acid aryl ester of formula (II) to be added; these solvents evaporate at the reaction temperature and thereby simultaneously serve as "entraining agents" for removing the hydrogen halide formed. It is also possible, and in many cases particularly advantageous, to carry out the reaction in an excess of the carbonic acid aryl ester halide of formula (III) as used as a reactant.

The process according to the invention is carried out without the addition of an acid-binding agent. However, it has proved advantageous for the hydrogen halide formed in the course of the reaction to be removed rapidly from the reaction mixture. This is most appropriately achieved by passing a continuous stream of air or nitrogen through the reaction mixture if the reaction is carried out in a high-boiling inert organic solvent or in excess carbonic acid aryl ester halide of formula (III) as the diluent. In contrast, it is not necessary additionally to pass a stream of air or nitrogen through the reaction mixture if a low-boiling solvent which, as mentioned above, functions as an "entraining agent" for removal of the hydrogen halide formed, is used.

The reaction temperatures can be varied within a substantial range. The reaction is in general carried out, as indicated above, between 100° and 300° C., preferably between 170° and 250° C.

If the reaction according to the invention is carried out in the presence of an inert organic solvent as the diluent, in general 1 to 15 moles, preferably 4 to 12 moles, of a carbonic acid aryl ester halide of the formula (III) are employed per mole of a carbamic acid aryl ester of the formula (II). In contrast, if an excess of carbonic acid aryl ester halide of formula (III) is used as the diluent, generally up to 80 moles, but appropriately about 5 to 40 moles and preferably about 10 to 25 moles, of carbonic acid aryl ester halide of formula (III) can be employed per mole of carbamic acid aryl ester of formula (II). It is thus advisable for the carbonic acid aryl ester halide of formula (III) in all cases to be employed in amounts which are greater than the stoichiometric amount.

The reaction products are isolated in a simple manner by separating the reaction mixture by distillation. Solid, higher-melting imido-dicarboxylic acid diaryl esters can also be easily purified by recrystallization.

The novel N-substituted imido-dicarboxylic acid diaryl esters according to the present invention can be used as intermediate products for the preparation of known herbicidal active compounds from the 1,3,5-triazine,2,4-(1H,3H)-dione series (see, for example, DE-OS (German Published Specification) No. 2,254,200 and U.S. Pat. No. 4,056,527).

According to a process which has not hitherto belonged to the state of the art (and which is the subject of a separate application for protection), 1,3,5-triazine-2,4-(1H,3H)-diones of the general formula

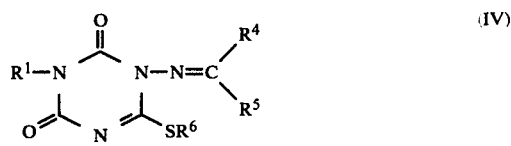

in which $R^1$ has the abovementioned meaning and $R^4$, $R^5$ and $R^6$ in each case represent identical or different alkyl radicals, can be prepared with a high yield and purity when the N-substituted imido-dicarboxylic acid diaryl esters according to the invention, of the general formula

in which $R^1$, $R^2$ and $R^3$ have the abovementioned meaning, are reacted with an isothiosemicarbazone of the general formula

in which $R^4$, $R^5$ and $R^6$ have the abovementioned meaning, in approximately stoichiometric amounts, without using a diluent and without adding a base as an auxiliary, at temperatures between 50° and 150° C., preferably between 70° and 120° C.

The triazinediones of formula (IV) can be worked up and isolated, for example, by a procedure in which the (optionally substituted) phenol or phenol mixture formed in the condensation reaction-(I)+(V)→(IV)-is distilled off in vacuo and the residue is purified, if necessary, by distillation under a high vacuum or by recrystallization.

The 1,3,5-triazine-2,4(1H,3H)-diones of formula (IV) thus prepared are themselves herbicidal active compounds; however, they can also be easily converted into the corresponding 1-amino-1,3,5-triazine-2,4(1H,3H)-diones of the general formula

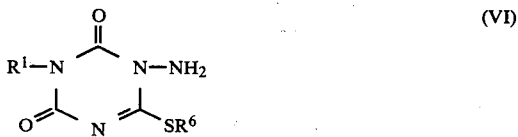

in which $R^1$ and $R^6$ have the abovementioned meaning, which are likewise excellent herbicides, by hydrolytic splitting off of the alkylidene radical (=CR$^4$R$^5$) which serves as a protective group. Furthermore, the S-alkyl radicals (—SR$^6$) in formulae (IV) and (VI) can be replaced by alkylamino or dialkylamino groups by reaction with primary or secondary amines, herbicidal active compounds which are also known being obtained (see likewise DE-OS (German Published Specification) No. 2,254,200 and U.S. Pat. No. 4,056,527).

The new process given here for the preparation of the herbicidal active compounds of the general formulae (IV) and (VI) and 6-amino-derivatives thereof, in which the imido-dicarboxylic acid diaryl esters of formula (I) according to the invention are used as starting compounds, has considerable and surprising advantages compared with the processes already known, for example DE-OS (German Published Specification) No. 2,254,200. Thus, the cyclization reaction can be carried out in the melt of the starting materials without using solvents. No other auxiliaries, such as, for example, organic bases, are required in this procedure. The only by-products are phenols (no hydrogen halides), which can easily be separated off and re-used. Finally, the imidodicarboxylic acid diaryl esters of formula (I) employed as starting substances can be prepared in high yields in an industrially simple manner from readily accessible precursors by the process claimed in the present application.

The isothiosemicarbazones of the general formula (V) are known or they can be prepared by known processes, for example by S-alkylation of thiosemicarbazones (see Houben-Weyl, Methoden der organischen Chemis (Methods of Organic Chemistry), 4th Edition, Volume 9, page 912).

The synthesis of the particularly effective herbicidal active compound 1-amino-6-ethylthio-3-neopentyl-1,3,5-triazine-2,4(1H,3H)-dione (the compound of formula (VIa) (see, for example Danish Patent Specification No. 136,067), starting from the compound N-neopentylimido-dicarboxylic acid diphenyl ester of formula (Ia) according to the invention, is described below by way of example; the course of the reaction can be represented by the following equation:

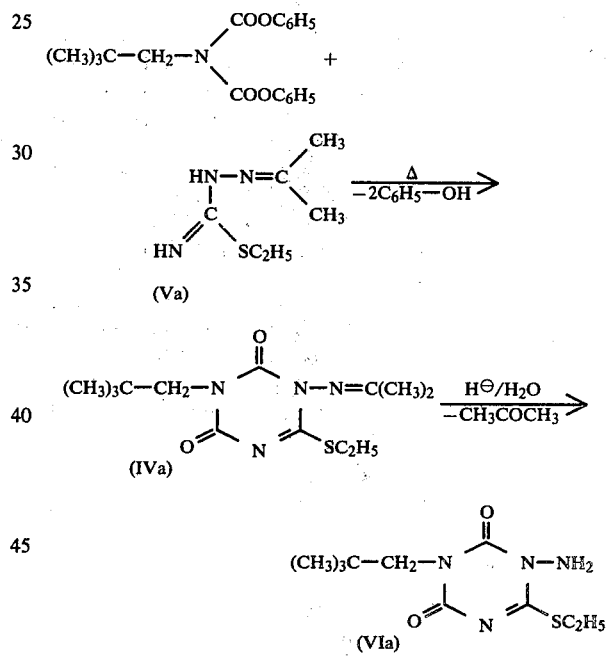

A mixture of 65.4 g (0.2 mole) of N-neopentylimido-dicarboxylic acid diphenyl ester (see Preparation Example 5) and 31.8 g (0.2 mole) of acetone S-ethylisothiosemicarbazone (the compound of formula (Va)) was melted under nitrogen and the melt was stirred at 100° C. for 5 hours. The phenyl formed was then distilled off in vacuo. The residue, which essentially consisted of 1-isopropylideneamino-6-athylthio-3-neopentyl-1,3,5-triazine-2,4(1H,3H)-dione (the compound of formula (IVa)), was dissolved in 200 ml of isopropanol. To split off the isopropylidene protective group hydrolytically, 2.8 g of p-toluenesulphonic acid were added, and 14.4 ml of water were added dropwise at a temperature of 60° C. and under a pressure of 200 to 300 mbar in the course of half an hour. The acetone formed was distilled off during the reaction, together with about 100 ml of isopropanol. The 1-amino-6-ethylthio-3-neopentyl-1,3,5-triazine-2,4(1H,3H)-dione (the compound of formula (VIa)) which had crystallized out was filtered off at 0° C. and washed with methanol. 38.2 g of (the compound of formula (VIa)) of melting point 202° C. were obtained, corresponding to a yield of 74% of theory.

Herbicidally active 1-amino-3-isobutyl-6-methylthio-1,3,5-triazine-2,4(1H,3H)-dione (the compound of formula (VIb)), which is known (see, for example, Danish Patent Specification No. 136,067) could be prepared in an analogous manner starting from the compound N-isobutylimido-dicarboxylic acid diphenyl ester (the compound of formula (Ib)) according to the invention, it being possible for the intermediate product 1-isopropylideneamino-3-isobutyl-6-methylthio-1,3,5-triazine,2-4(1H,3H)-dione (the compound of formula (IVb)) to be isolated.

1st stage:

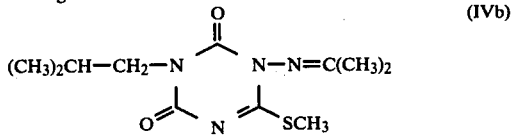

34.6 g (0.11 mole) of N-isobutyl-imido-dicarboxylic acid diphenyl ester (the compound of formula (Ib)) (see Preparative Example 3) and 16.0 g (0.11 mole) of acetone S-methyl-isothiosemicarbazone were melting at 50° C. and the melt was stirred for 4 hours in an oil bath of 100° C. The phenol formed was distilled off under a pressure of 18 mbars, the bath temperature being increases to 140° C. The residue (30.3 g) solidified; it was boiled up with 150 ml of cyclohexane, 22.4 g of pure 1-isopropylideneamino-3-isobutyl-6-methylthio-1,3,5-triazine-2,4(1H,3H)-dione (the compound of formula (IVb)) of melting point 125° to 127° C. remaining as undissolved material. A further 6.4 g of the compound of formula (IVb) crystallized from the filtrate of the mixture. The total yield was 28.8 g (97% of theory). The compound of formula (IVb) could be distilled: boiling point: 165° C. under 0.38 mbar.

2nd stage:

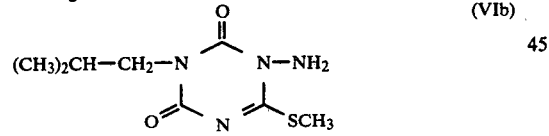

27.0 g (0.1 mole) of the compound of formula (IVb) were dissolved in 200 ml of isopropanol at 60° C. in a distillation apparatus and a pressure of 260 to 200 mbars was established, so that the solvent started to boil and was condensed in the descending condenser. The internal temperature was 45° to 50° C. A solution of 0.4 ml of concentrated sulphuric acid in 7 ml of water was then added dropwise in the course of 15 minutes, about 70 ml of isopropanol, together with the acetone formed, being distilled off during this period. 14.5 g of 1-amino-3-isobutyl-6-methylthio-1,3,5-triazine-2,4(1H,3H)-dione (the compound of formula (VIb)) of melting point 167° to 169° C. crystallized out, at 0° C., from the solution which remained; a further 4.5 g were obtained from the concentrated filtrate of the mixture. The total yield of 19.0 g corresponding to 83% of theory.

The Preparative Examples which follow are illustrated processes for the production of compounds of the invention in more detail.

Example 1

600 ml (4.72 moles) of carbonic acid phenyl ester chloride were brought to the boil in a 4-necked flask provided with a stirrer, gas inlet tube, reflux condenser and dropping funnel while passing through a stream of air or nitrogen. A solution of 71.6 g (0.4 mole) of isopropyl-carbamic acid phenyl ester (melting point: 78° to 80° C.) in 300 ml of carbonic acid phenyl ester chloride (2.36 moles) was then uniformly added dropwise at an internal temperature of 180° to 185° C. in the course of 5 hours, during which air or nitrogen was further passed through the reaction solution for rapid removal of the hydrogen chloride formed. The mixture was subsequently stirred for a further 2 hours at the boiling point, the excess carbonic acid phenyl ester chloride was distilled off at a bath temperature of 140° C. and under a pressure of 20 mbars and the residue was distilled in vacuo.

57.9 g of N-isopropyl-imido-dicarboxylic acid diphenyl ester with a boiling point of 155° C./0.07 mbar and a melting pont of 35° to 37° C. were obtained. The purity, determined by gas chromatography, was 98%; this corresponded to a yield of 47% of theory.

Example 2

77.2 g (0.4 mole) of tert.-butyl-carbamic acid phenyl ester (melting point: 92° C.) were reacted with excess carbonic acid phenyl ester chloride (4.72 moles) as descrined in Example 1 and, after working up, 26.4 g of N-tert.-butyl-imido-dicarboxylic acid diphenyl ester with a boiling point of 150° C./0.1 mbar and a melting point of 132° C. (from ethyl acetate) were obtained.

The purity, determined by gas chromatography, was 99.7%; this corresponded to a yield of 21% of theory.

Example 3

77.2 g (0.4 mole) of isobutyl-carbamic acid phenyl ester (melting point: 67° C.) were reacted with excess carbonic acid phenyl ester chloride (4.72 moles) analogously to Example 1. After the distillation, 102.4 g of N-isobutyl-imido-dicarboxylic acid diphenyl ester with a boiling point of 160° C./0.1 mbar and a purity of 93.7% were obtained. After recrystallizing from about 500 ml of petroleum ether, filtering off the crystals at −70° C. and washing them with intensely cooled petroleum ether, 88 g of the given compound with a melting point of 40° C. and a purity of 100%, corresponding to 70% of theory, were obtained.

Example 4

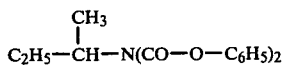

77.2 g (0.4 mole) of sec.-butyl-carbamic acid phenyl ester (melting point: 43° C.) were reacted with excess carbonic acid phenyl ester chloride (4.72 moles) analogously to Example 1. After working up, 45.8 g of N-sec.-butyl-imido-dicarboxylic acid diphenyl ester with a boiling point of 165°–170° C./0.2 mbar and a refractive index $n_D^{20}$ of 1.5336 were obtained. The purity, determined by gas chromatography, was 97.8%, corresponding to a yield of 36% of theory.

Example 5a

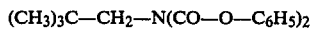
(CH₃)₃C—CH₂—N(CO—O—C₆H₅)₂

A solution of 331 g (1.6 moles) of neopentylcarbamic acid phenyl ester in 1,000 g (6.39 moles) of carbonic acid phenyl ester chloride was added dropwise to 4,000 g (25.56 moles) of boiling carbonic acid phenyl ester chloride, through which a vigorous stream of nitrogen was passed, in the course of 5 hours. The overhead temperature in the reflux condenser was kept at 80° to 90° C., so that the small amount of neopentyl isocyanate formed as the by-product could be distilled off over the top with the stream of nitrogen and condensed in a subsequent descending condenser. (After reaction with phenol to give neopentyl-carbamic acid phenyl ester, it was then passed again to the reaction). The mixture was subsequently stirred for 4 hours, while passing further nitrogen through, the excess carbonic acid phenyl ester chloride was then distilled off at a bath temperature of 140° C. and under a pressure of 20 mbars and the residue was distilled from a heating bath of 170° C. until a boiling point of 150° C. under a pressure of 0.6 mbar was reached. The residue consisted of 96.5% pure N-neopentyl-imido-dicarboxylic acid diphenyl ester. Yield: 489 g (90% of theory). A sample recrystallized from petroleum ether melted at 81° C. The substance could be distilled: boiling point: 156° C./0.02 mbar.

The neopentyl-carbamic acid phenyl ester which was used as the starting material and is novel, could be prepared, for example, as follows, starting from neopentylamine:

A solution of 80 g (2 moles) of sodium hydroxide and 176 g (2 moles) of 90% pure neopentylamino in 3.4 liters of water was added dropwise to a solution of 329 g (2.1 moles) of carbonic acid phenyl ester chloride in 1 liter of toluene, while stirring vigorously. An internal temperature of 10° to 20° C. was maintained by cooling. When the reaction had ended, the phases were separated, the organic phase was washed with water and filtered and the filtrate was evaporated to dryness. 408 g of a 97% pure crude product (95.6% of theory) which had a melting point of 69° to 72° C. and was sufficiently pure for further reactions were obtained. After recrystallizing from 2 liters of petroleum ether, 365 g, of melting point 77° to 78° C., were obtained.

Example 5b

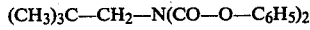
(CH₃)₃C—CH₂—N(CO—O—C₆H₅)₂ variant of the process of Example 5a.

414 g (2 moles) of neopentyl-carbamic acid phenyl ester were uniformly added dropwise as a melt, from a dropping funnel heated to 120° C., to 2.54 liters (20 moles) of boiling carbonic acid phenyl ester chloride in the course of 8 hours, while passing through a vigorous stream of nitrogen. The mixture was worked up analogously to Example 5a and 510 g of 98% pure N-neopentylimido-dicarboxylic acid diphenyl ester were obtained. A further 37 g of the same product could be obtained by working up the portion which distilled between 120° and 150° C. under 0.6 mbar.

The total yield was 82% of theory of N-neopentylimido-dicarboxylic acid diphenyl ester.

The neopentyl-carbamic acid phenyl ester used as the starting material was prepared by another process as follows:

2,140 g (10 moles) of carbonic acid diphenyl ester were melted at 80° C. 870 g (10 moles) of neopentylamine were added dropwise at this temperature in the course of 3 hours, the phenol formed was distilled off in vacuo and the residue was recrystallized from petroleum ether. 1,725 g (83% of theory) of neopentyl-carbamic acid phenyl ester of melting point 77° to 78° C. were obtained.

Example 5c

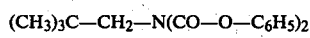
(CH₃)₃C—CH₂—N(CO—O—C₆H₅)₂ variant of the process of Examples 5a and 5b.

A 4 liter three-necked flask was provided with a stirrer and reflux condenser. A Reitmeir attachment connected to a descending distillation bridge with an intensive condenser was fitted to the reflux condenser. A special gas inlet frit, to which a dropped funnel was attached via a ground glass joint was immersed in the stirred flask. The gas inlet tube of the frit was connected to the dropping funnel for pressure compensation. The reflux condenser was charged with water of 80° to 95° C. and the descending condenser was charged with cold water.

2.54 liters (20 moles) of carbonic acid phenyl ester chloride were then heated to the boiling point in the stirred flask. A solution of 414 g (2 moles) of neopentyl-carbamic acid phenyl ester in 300 ml of methylene chloride were then uniformly added dropwise into the gas inlet frit at a bottom temperature of 185° to 190° C. in the course of 9 hours, the hydrogen chloride formed being immediately removed from the reaction medium by the evaporating solvent. The solvent was condensed in the intensive condenser and the hydrogen chloride entrained was absorbed in water in a downstream wash tower. The boiling carbonic acid phenyl ester chloride was in this manner condensed in the reflux condenser and was prevented from being entrained with the methylene chloride vapor by the Reitmeir attachment.

The mixture was worked up analogously to Example 5a and a total of 581 g of 98% pure N-neopentyl-imido-dicarboxylic acid diphenyl ester, corresponding to a yield of 87% of theory, was obtained.

Example 6

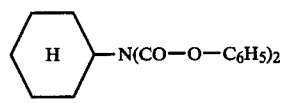

A solution of 87.6 g (0.4 mole) of cyclohexylcarbamic acid phenyl ester (melting point: 136° to 137° C.) in 1,000 g (6.4 moles) of carbonic acid phenyl ester chloride was added dropwise to 750 g (4.8 moles) of boiling carbonic acid phenyl ester chloride and the mixture was boiled under reflux for a further 3 hours, while passing nitrogen through, and was worked up analogously to Example 1.

83.1 g of N-cyclohexyl-imido-dicarboxylic acid diphenyl ester with a boiling range of 165° to 175° C. under 0.1 mbar and a purity, determined by gas chromatography, of 97.5% were obtained. A sample recrystallized from petroleum ether melted at 85° C. Yield: 60% of theory.

Example 7

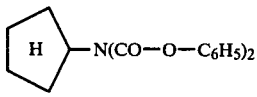

83.0 g (0.4 mole) of cyclopentylcarbamic acid phenyl ester (melting point: 115°–117° C.) were reacted with excess carbonic acid phenyl ester chloride (a total of 8.8 moles) analogously to Example 6. 81.2 g of N-cyclopentyl-imido-dicarboxylic acid diphenyl ester with a boiling range of 155° to 182° C. under 0.1 mbar and a purity, determined by gas chromatography, of 86.8%, corresponding to a yield of 54.2% of theory, were obtained. After recrystallizing from 300 ml of petroleum ether, 52 g of melting point 53° C. were obtained.

Example 8

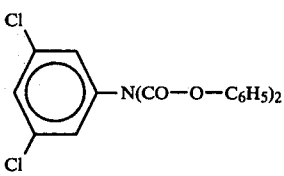

A solution of 56.4 g (0.2 mole) of 3,5-dichlorophenylcarbamic acid phenyl ester (melting point: 141° C.) in 1,015 ml (8.0 moles) of carbonic acid phenyl ester chloride were added dropwise to 306 ml (2.4 moles) of boiling carbonic acid phenyl ester chloride in the course of 5 hours. During this addition, nitrogen was passed through the reaction solution. The mixture was then boiled under reflux for a further 4 hours and the excess carbonic acid phenyl ester chloride was distilled off at a bath temperature of 140° C. and under a pressure of 20 mbars. The residue contained 3,5-dichlorophenyl isocyanate and diphenyl carbonate as impurities.

These impurities were largely distilled off at a bath temperature of 150° C. and under a pressure of 0.3 mbar. The distillation residue was recrystallized from 300 ml of ethyl acetate. 15.6 g (19.4% of theory) of N-(3,5-dichlorophenyl)-imido-dicarboxylic acid diphenyl ester of melting point 178° to 180° C. were obtained.

Example 9

(C$_2$H$_5$)$_2$CH—N(CO—O—C$_6$H$_5$)$_2$

A solution of 82.8 g (0.4 mole) of (1-ethyl-propyl)carbamic acid phenyl ester (melting point: 65° to 67° C.) in 500 ml (3.9 moles) of carbonic acid phenyl ester chloride was added dropwise to 600 ml (4.7 moles) of boiling carbonic acid phenyl ester chloride in the course of 5 hours, a vigorous stream of nitrogen being passed through the boiling solution during this addition. The mixture was boiled under reflux for a further 4 hours, the excess carbonic acid phenyl ester chloride was distilled off in vacuo and the reaction was distilled under a high vacuum.

84.6 g (64.7%) of N-(1-ethyl-propyl)-imido-dicarboxylic acid diphenyl ester with a boiling point of 134° C./0.09 mbar and a melting point of 54° to 56° C. (from pentane) were obtained.

Example 10

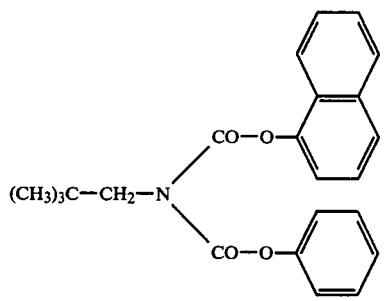

A solution of 59.1 g (0.23 mole) of neopentylcarbamic acid α-naphthyl ester (melting point: 116° to 117° C.) in 600 ml (4.7 moles) of carbonic acid phenyl ester chloride were added dropwise to 300 ml (2.35 moles) of boiling carbonic acid phenyl ester chloride in the course of 5 hours, during which, a vigorous stream of nitrogen was passed through the solution. After distilling off the excess carbonic acid phenyl ester chloride, the residue which remained (83.0 g, 95.4% pure according to the gas chromatogram—corresponding to a yield of 91.3%) was distilled under a high vacuum.

52.7 g of N-neopentyl-imido-dicarboxylic acid phenyl α-naphthyl ester of boiling point 230° to 235° C./0.25 mbar were obtained.

Example 11

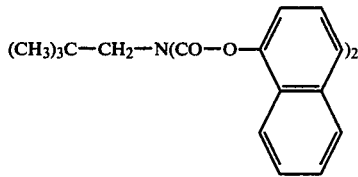

A solution of 29.4 (0.114 mole) of neopentylcarbamic acid α-naphthyl ester (melting point: 117° to 118° C.) in 510 g (2.47 moles) of carbonic acid α-naphthyl ester chloride were added dropwise to 250 g (1.21 moles) of carbonic acid α-naphthyl ester chloride, heated to 230° to 240° C., in the course of 5 hours, during which a vigorous stream of air was passed through the solution. The mixture was stirred at 240° C. for a further 4 hours, whilst passing further air through, the excess carbonic acid α-naphthyl ester was distilled off (boiling point: 155° C. under 20 mbars) and the traces still present were then removed by heating the residue to 140° C. under 0.03 mbar.

The residue (49 g) was recrystallized twice from in each case 500 ml of petroleum ether.

22.9 g (47%) of N-neopentyl-imido-dicarboxylic acid di-α-naphthyl ester of melting point 92°–93° C. were obtained.

Example 12

CF₃—CH₂—N(CO—O—C₆H₅)₂

21.9 g (0.1 mole) of 2,2,2-trifluoroethylcarbamic acid phenyl ester (melting point: 88° to 90° C.) are introduced into 85 ml (0.67 mole) of carbonic acid phenyl ester chloride and the mixture was heated under reflux for 20 hours. After distilling off the excess carbonic acid phenyl ester chloride, the residue was subjected to incipient distillation over a short Vigreux column until the boiling point reaches 132° C. under 0.1 mbar. 28.7 g of crude product which, according to the gas chromatogram, consisted of 98% pure N-(2,2,2-trifluoroethyl)-imido-dicarboxylic acid diphenyl ester (corresponding to a yield of 83% of theory) were obtained as the residue. A sample recrystallized from wash benzine melted at 76° C. The boiling point was 140° C. under 0.3 mbar.

It will be understood that the specification and examples are illustrative but not limitative of the present invention and that other embodiments within the spirit and scope of the invention will suggest themselves to those skilled in the art.

What is claimed is:

1. N-substituted imido-dicarboxylic acid diaryl ester compound of the formula

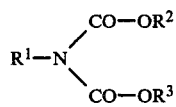  (I)

wherein
R¹ is a straight-chain or branched aliphatic radical which has 3 to 5 carbon atoms; a straight-chain or branched aliphatic radical which has 2 to 5 carbon atoms and substituted by lower alkoxy, lower alkylmercapto, halogen, cyano or nitro; or a cycloaliphatic radical which has 5 to 8 carbon atoms and is optionally substituted by lower alkyl; and
R² and R³ independently represent a phenyl or naphthyl radical which is optionally substituted by chlorine, methyl and/or methoxy.

2. N-substituted imido-dicarboxylic acid diaryl ester compound selected from the group consisting of (CH₃)₃C—CH₂—N(CO—O—C₆H₅)₂,

CF₃—CH₂—N(CO—O—C₆H₅)₂, (CH₃)₂CH—CH₂—N(CO—O—C₆H₅)₂,

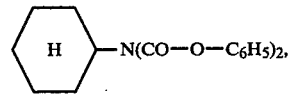

and (CH₃)₂CH—N(CO—OC₆H₅)₂.

3. N-substituted imido-dicarboxylic acid diaryl ester compound as claimed in claim 2 wherein said compound is (CH₃)₃C—CH₂N(CO—O—C₆H₅)₂

4. N-substituted imido-dicarboxylic acid diaryl ester compound as claimed in claim 2 wherein said compound is

CF₃—CH₂—N(CO—O—C₆H₅)₂

5. N-substituted imido-dicarboxylic acid diaryl ester compound as claimed in claim 2 wherein said compound is (CH₃)₂CH—CH₂—N(CO—O—C₆H₅)₂

6. N-substituted imido-dicarboxylic acid diaryl ester compound as claimed in claim 2 wherein said compound is

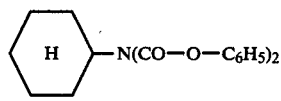

7. N-substituted imido-dicarboxylic acid diarylester as claimed in claim 2 wherein said compound is (CH₃)₂CH—N(CO—OC₆H₅)₂.

8. The N-tert.-butyl-imido-dicarboxylic acid diphenyl ester of the formula (CH₃)₃C—N(CO—OC₆H₅)₂.

9. The N-sec.-butyl-imido-dicarboxylic acid diphenyl ester of the formula

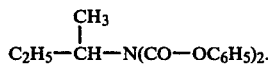

10. The N-cyclopentyl-imido-dicarboxylic acid diphenyl ester of the formula

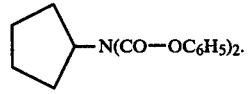

11. The N-(1-ethylpropyl)-imido-dicarboxylic acid diphenyl ester of the formula

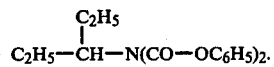

12. The N-neopentyl-imido-dicarboxylic acid α-naphthyl phenyl ester of the formula

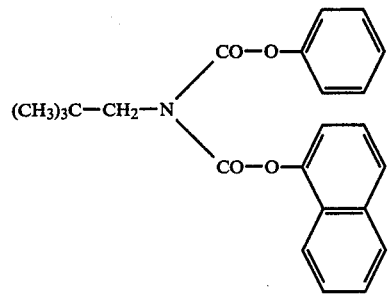

13. The N-neopentyl-imido-dicarboxylic acid di-α-naphthyl ester of the formula

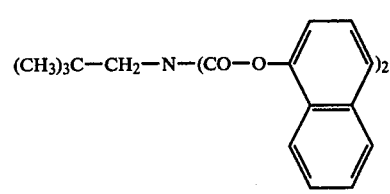

* * * * *